United States Patent [19]

Törnqvist

[11] Patent Number: 4,818,115
[45] Date of Patent: Apr. 4, 1989

[54] DEVICE TO MECHANICALLY BREAK APART A BARRIER

[76] Inventor: Peter J. T. Törnqvist, Barkassvägen 11, S-181 35 Lidingö, Sweden

[21] Appl. No.: 876,872
[22] PCT Filed: Oct. 2, 1985
[86] PCT No.: PCT/SE85/00381
  § 371 Date: May 29, 1986
  § 102(e) Date: May 29, 1986
[87] PCT Pub. No.: WO86/01995
  PCT Pub. Date: Apr. 10, 1986

[30] Foreign Application Priority Data

Oct. 2, 1984 [SE] Sweden .................... 8404931

[51] Int. Cl.⁴ .................... B01F 11/00; A61C 5/06
[52] U.S. Cl. .................... 366/212; 366/111; 366/124; 366/240; 366/602
[58] Field of Search ............ 366/602, 240, 332, 250, 366/212, 349, 208–210, 108, 110, 111, 112, 114, 116, 124, 237, 202–204; 206/219, 220, 221

[56] References Cited

U.S. PATENT DOCUMENTS

| | | | |
|---|---|---|---|
| 1,421,016 | 6/1922 | Leipold | 366/210 |
| 1,704,010 | 3/1929 | Manon et al. | 366/212 |
| 3,198,502 | 8/1965 | Thompson | 366/332 |
| 3,240,403 | 3/1966 | Modderno | 206/221 |
| 3,263,970 | 8/1966 | Steinbock et al. | 366/279 |
| 3,275,302 | 9/1966 | Horton | 366/209 |
| 3,727,890 | 4/1973 | Seidl et al. | 366/116 |
| 3,749,390 | 7/1973 | Schubert | 366/602 |

FOREIGN PATENT DOCUMENTS 2254486 6/1973 Fed. Rep. of Germany .
2745476 5/1978 Fed. Rep. of Germany .

Primary Examiner—Harvey C. Hornsby
Assistant Examiner—Joseph S. Machuga
Attorney, Agent, or Firm—Frishauf, Holtz, Goodman & Woodward

[57] ABSTRACT

A device to mechanically decompose a barrier which separates two or more mutually miscible ingredients and mixes the said ingredients, preferably a mixer for amalgam in capsules. The device 1 comprises first members to fixedly hold the said ingredients and second members to impart to the said ingredients a sufficiently rapid motion to accomplish the said barrier decomposition and mixing.

The said first members comprise a closable space 4 into which the said ingredients and said capsule 2 respectively are admissible and by which these or this respectively is or are respectively aligned with the said second members 14, 15. The said second members 14, 15 are arranged to be started only upon or after closing of the said closable space 4.

13 Claims, 2 Drawing Sheets

DEVICE TO MECHANICALLY BREAK APART A BARRIER

BACKGROUND OF THE INVENTION

This invention relates to a device to mechanically decompose a barrier which separates two or more mutually miscible ingredients and to mix the said ingredients, preferably a mixer for amalgam in capsules, the said device comprising first members to fixedly hold the said ingredients and second members to impart to the said ingredients a sufficiently rapid motion to accomplish the said barrier decomposition and mixing.

Known amalgam mixers are usually very large and clumsy, are driven electrically, vibrate powerfully and have a high noise level, as well as requiring accurate fixation of the capsule in which the mixable amalgam is located. Further, known mixers are usually placed so that the dentist is obliged to interrupt the work he is doing in order to move to the mixer, to insert an amalgam capsule and to stop the machine. Only after this can the dentist or dental nurse return to the interrupted work. When mixing of the amalgam is ready the dentist or nurse must once again interrupt what he or she is doing and walk to the mixer, remove the capsule and return to the patient. This walking back and forth repeatedly makes demands on the time not only of the dentist or nurse but also of the patient and thus costs large sums of money.

Known amalgam mixers also call for a relatively careful location and alignment and fixation of the capsule, which actions also take unnecessary and expensive time.

An object of the present invention is to provide a device which is simple and quick to use, which is quiet-running, which gives low or no self-propagating vibrations and which is small in size and thus possible to place in a suitable position in relation to the dentist and which is relatively simple and thus can be manufactured at a favourable price.

The invention is characterized in the type of device mentioned in the descriptive preamble in that the said first members comprise a closable space in which the said ingredients and said capsule respectively ar miscible and of which these and this respectively are aligned with the said second members, and in that the said second members are arranged to be started only when or after closing of the said closable space. In particular the invention, where the said second members comprise a piston and a return-fed sleeve with bottom, is characterized in that the said piston is arranged to be driven reciprocatingly largely in a rectilinear motion, in that the said return-fed sleeve with bottom is arranged to move essentially in the same motional direction as the piston and in that the said ingredients and capsule respectively are arranged placeable between the piston and the sleeve with bottom.

BRIEF DESCRIPTION OF THE DRAWINGS

The invention will now be described in more detail below and with reference to the accompanying drawings, wherein.

DETAILED DESCRIPTION OF THE PREFERRED EMBODIMENT

Figure 1:
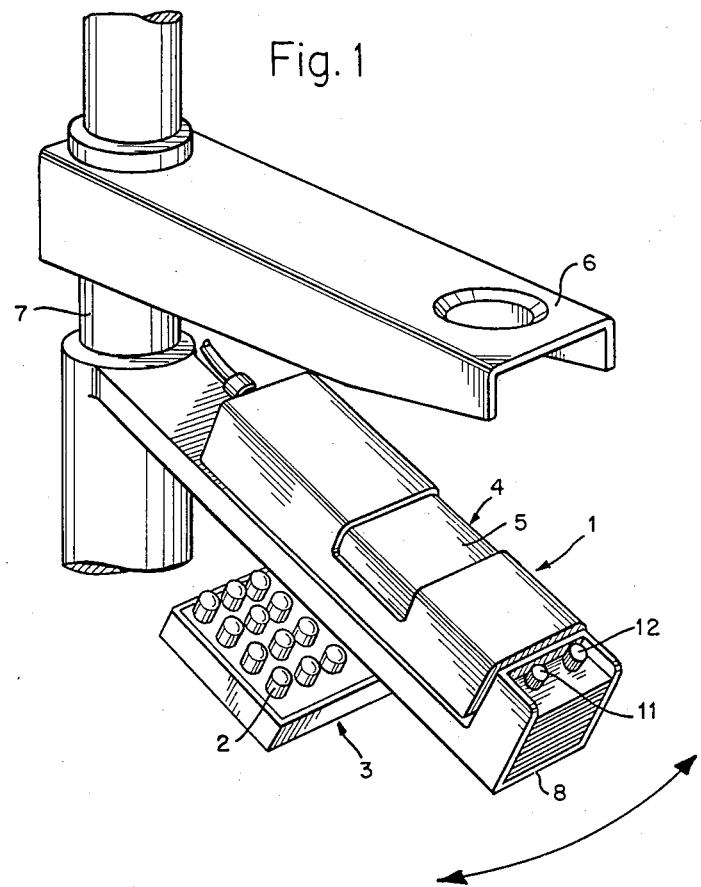
FIG. 1 shows a perspective view of the device in the invention placed as an example at the dentist's working place.
Figure 2:
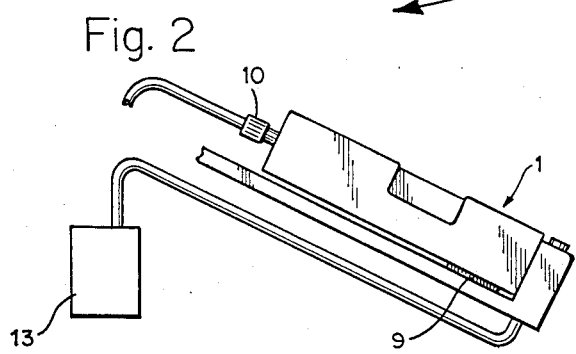
FIG. 2 shows how the device according the invention can be quickly mounted and removed for the purpose of facilitating cleaning thereof and FIG. 3 shows an embodiment of the device according to the invention selected as an example.

The device according to the invention is sited advantageously to close to the dentist that he reaches the amalgam mixer 1 without any problems and can admit a capsule 2 from a capsule rack 3 located at the side of the mixer into a space 4 provided in the mixer 1, the said space being closable by means of a movable cover 5 and provided with, not closely illustrated, for example bowl-shaped sides to conduct the admitted capsule 2 to the wanted position in the space 4.

The device can for example be located below the arm 6 which supports the saliva suction device relative to a vertical post 7 of a dental chair and is supported rotatably relative to the latter by an arm 8 which is equipped to advantage with for instance a magnet 9 to hold the device in position relative to the arm 8 and with a quick-coupling 10 for connection of for instance compressed air to the device. Compressed air is normally already run to the dental chair to power other tools, so that the power medium fo the device is already available in the chair.

By means of an appropriately selected timer the requisite mixing time can be selected with a settable key 11, while a second key 12 comprises a start button for the device according to the invention. The timer 11 in its turn controls for instance a solenoid valve 13 which when activated admits compressed air to the device.

Figure 3:
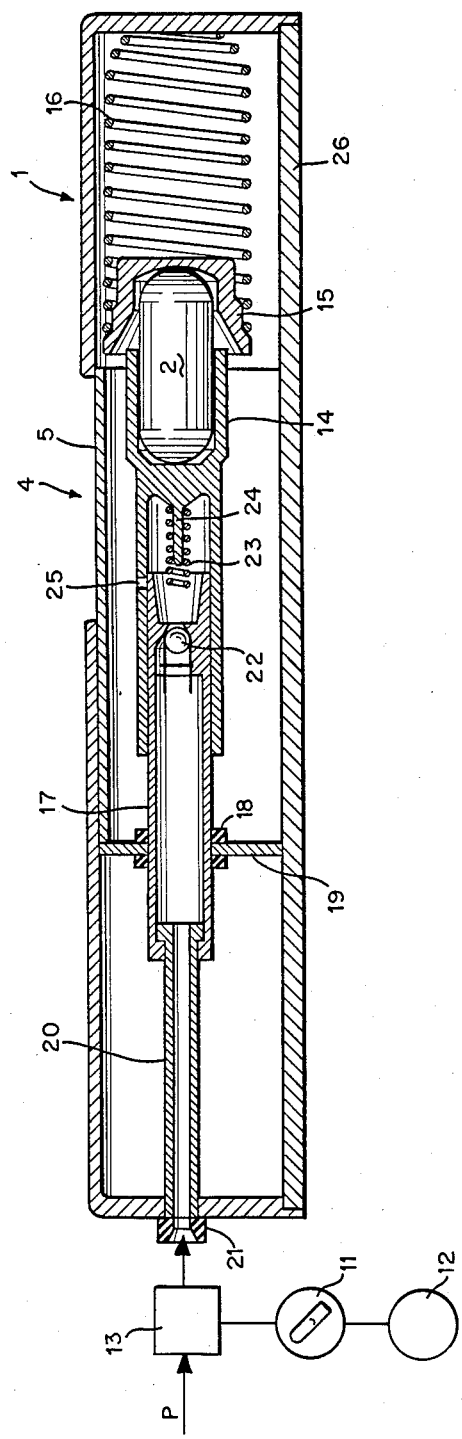

A selected embodiment of the device according to the invention is illustrated in cross-section by FIG. 3. The movable lid 5—in unactuated condition—is positioned to the left in the figure; in other words the space 4 is open. A capsule 2 containing or provided with the ingredients which are to form the finished amalgam in mixed condition and which are separated by a barrier are released or placed by the dentist in the open space 4 and fall, guided by the side walls of the space 4 down into position between a bowl-shaped piston 14 and a cup 15 facing piston 14, the said cup 15 being fed to the left by for instance a spring 16, by compressed air or in some suitable manner.

The piston 14 is movably arranged and supported relative to a tube 17 which in turn is fixed to advantage via a rubber bush 18 in a vertical wall 19, mechanically coupled to the lid 5. The movable tube 17 interacts with the stationary tube 20 which preferably via a rubber bush 21 is fixed in the device 1. Compressed air P is connected to the left—seen in FIG. 3—end of the stationary tube 20 by a valve 13, appropriately a solenoid valve, which is controlled by the timer 11 to be open for a time settable on the timer, which for example can be selected to be between 5–120 seconds. The timer 1 is started to advantage with the start key 12.

The device according to the invention functions in the following manner. The capsule 2 from the capsule rack 3 is admitted into the open space 4 and drops down into the correct intended position. The wanted mixing time is set on the timer 11 whereupon the start key 12 is activated and the device 1 receives via the then open solenoid valve 13 compressed air P to the interior of the stationary tube 20, whereupon the interior of the movable tube 17 also becomes pressurized. A ball 22 in the right—seen in FIG. 3—end of the movable pipe 17 is pressed by the pressure P against a seat, whereby the movable pipe 17 accompanied by the lid 5 and piston 14 is driven to the right in FIG. 3 all the way until the lid 5 is fully closed and the space 4 is thereby sealed.

The cup 15 and thus the inserted capsule 2 are moved by the spring 16 to the left to FIG. 3 and the bowl of the piston 14 catches the left part of the capsule 2 at a distance from the cup 15, whereby the piston 14 is moved via the capsule 2 to the left so far that via a post 24 and a spring 23 it actuates the ball 22 to admit compressed air P to the piston 14, which is thereby driven to the right in FIG. 3 by the compressed air P all the way until a release 25 in the piston 14 is uncovered and the pressure drops. The said pressure release can be used if so desired or required to cool the capsule 2 and thus the capsule mixture. The capsule 2 now returns the piston 14 to the left on account of the action of the spring 16 and the procedure is repeated so that the capsule 2 is thereby imparted a reciprocating motion during a time determined by the timer 11.

When the timer 11 closes the supply of compressed air P the lid 5 is opened by the action of the spring 16 via the cup 15, via the capsule 2, via the piston 14 and via the movable tube 17, whereby the capsule 2 with the ready-mixed amalgam mixture becomes available from outside and can be lifted up.

The object of the spring 23 is to ensure that the ball 22 is unable to occupy any stable open intermediate position but that the ball 22 either closes under the influence of pressure or is opened by the post 24.

In the embodiment shown in FIG. 3 the capsule 2 is imparted a rectilinear motion reciprocatingly but obviously it is also possible by means of appropriate resilient suspension and adaption of the weights of different parts to give the capsule 2 a motion that resembles a recumbent eight if so should be desired.

The device 1 according to the invention is equipped to advantage with a heavy bedplate 26, the mass of which is large in relation to the moving parts in the device 1 and the capsule 2, whereby any vibrations that occur do not influence the position of the device 1 or are propagated outside the device 1 to any appreciable extent.

The expression timer hereintofor obviously also includes all known means of determining running time or the number of strokes performed by the device 1. For example the number of strokes can be sensed by means of a photocell, an inductive transducer, by means of some kind of balance wheel, by means of compressed air, by means of a travelling movement for the piston 14 and the tube 17 etc.

In the embodiment illustrated in FIG. 3 the compressed air admission P has been placed in line with the tube 17 and the piston 14 but obviously the supply of power medium can instead taken place via for example a flexible hose, whereby the device 1 can be made shorter essentially corresponding to the length of the tube 20.

Other modifications and variations respectively are obviously possible within the scope of the accompanying claims.

An alternative embodiment in which valve 13, timer 11 and key 12 can be excluded, is that the lid 5 is instead moved manually to a closed position to the right in FIG. 3 where the lid 5 and accompanying parts are arrested via for example a mechanical or pneumatical time-regulating device.

I claim:

1. Apparatus for vibrating a device containing a barrier separating at least two mutually miscible ingredients for breaking the barrier and subsequently mixing said ingredients, comprising:
   an enclosure having walls defining a space sized such as to accommodate said device, at least one of the walls defining said space being an outer wall of said enclosure;
   an opening defined in said outer wall and being sized to admit said device therethrough, said space being in communication with the exterior of said enclosure through said opening;
   a lid coupled to said enclosure for movement between a first position closing said opening and a second position uncovering said opening;
   means for moving said lid between its first and second positions;
   means for imparting to said device a sufficiently rapid vibratory motion within said space to break said barrier and mix said substances, and for actuating said vibratory motion upon said lid closing said opening.

2. The apparatus of claim 1, wherein said vibratory motion imparting means comprises:
   a resilient means secured within said enclosure for biasing said device in a given direction;
   a pressure-actuated means for moving said device against the bias of said resilient means; and
   cycling means for (a) applying fluid pressure to said pressure-actuated means of a preset magnitude for moving said device against a biasing force to said resilient means, (b) then sufficiently relieving said fluid pressure to a level such that the resilient means moves the device in said given direction, (c) re-establishing the preset magnitude of fluid pressure and (d) repeating (a)–(c).

3. The apparatus of claim 2, wherein said pressure-actuated means comprises a first piston slidably coupled within said enclosure to move along a line substantially parallel to said given direction.

4. The apparatus of claim 3, wherein said cycling means comprises an opening in a head of said piston to which said fluid pressure is applied, and displaceable sealing means for sealing said piston head opening, a second piston within which said first piston is slidably received, said second piston being movable along said parallel line, a release outlet defined in said second piston and positioned to become uncovered only when said second piston extends a pre-selected distance beyond said first piston toward said resilient means, and engagement means on said second piston for displacing said sealing means away from said piston head opening when said first piston is in a pre-selected telescoped position within said second piston, said release outlet being covered when the engagement means is in contact with the sealing means, and said sealing means being spaced from said engagement means when the release outlet is uncovered.

5. The apparatus of claim 4, wherein said cycling means further comprises a second resilient means between the first and second piston for biasing said first piston in the given direction and for biasing said second piston in an opposite direction.

6. The apparatus of claim 5, wherein said lid is secured to said first piston for sliding motion therewith within said enclosure.

7. The apparatus of claim 6, wherein movement of the first piston and second piston toward the resilient means along said parallel line is such as to cause the resilient means to generate a sufficient force to move the device in said given direction only upon the first piston being so positioned as to place said lid in its first position.

8. The apparatus of claim 7, wherein said device is retained in a holder within said space, said holder having one part thereof engaging said second piston, and another part thereof engaging said resilient means.

9. The apparatus of claim 2, wherein said means for applying fluid pressure comprises a valve actuated by a timer.

10. The apparatus of claim 3, wherein said lid is secured to said first piston for sliding motion therewith within said enclosure.

11. The apparatus of claim 10, wherein movement of the first piston and second piston toward the resilient means along said parallel line is such as to cause the resilient means to generate a sufficient force to move the device in said given direction only upon the first piston being so positioned as to place said lid in its first position.

12. The apparatus of claim 4, wherein movement of the first piston and second piston toward the resilient means along said parallel line is such as to cause the resilient means to generate a sufficient force to move the device in said given direction only upon the first piston being so positioned as to place said lid in its first position.

13. The apparatus of claim 4 wherein said device is retained in a holder within said space, said holder having one part thereof engaging said second piston, and another part thereof engaging said resilient means.

* * * * *